United States Patent [19]

Citri

[11] Patent Number: 5,369,013
[45] Date of Patent: Nov. 29, 1994

[54] METHOD, REAGENT MIXTURE AND KIT FOR DETERMINING THE PRESENCE OF BACTERIAL OR SOMATIC CELLS IN URINE

[75] Inventor: Nathan Citri, Jerusalem, Israel

[73] Assignee: Yissum Research Development Company of the Hebrew University of Jerusalem, Israel

[21] Appl. No.: 919,925

[22] Filed: Jul. 27, 1992

Related U.S. Application Data

[63] Continuation-in-part of Ser. No. 676,864, Mar. 28, 1991, abandoned, which is a continuation of Ser. No. 548,023, Jul. 5, 1990, abandoned, which is a continuation of Ser. No. 65,315, Jun. 22, 1987, abandoned.

[51] Int. Cl.$^5$ ............... C12Q 1/30; C12Q 1/62; C12Q 1/44
[52] U.S. Cl. .............. 435/27; 435/10; 435/19; 435/23; 435/810
[58] Field of Search ............ 435/10, 19, 23, 27, 435/810

[56] References Cited

U.S. PATENT DOCUMENTS

| | | | |
|---|---|---|---|
| 3,764,479 | 10/1973 | Bergeron | 435/12 |
| 3,853,471 | 12/1974 | Rittersdorf | 436/66 |
| 3,853,472 | 12/1974 | Rittersdorf | 436/66 |
| 4,116,773 | 9/1978 | Polito | 195/99 |
| 4,311,794 | 1/1982 | Melnick et al. | 435/32 |
| 4,314,030 | 2/1982 | Habich | 435/296 |
| 4,481,294 | 11/1984 | Downs | 435/259 |

FOREIGN PATENT DOCUMENTS 36496  6/1974  Israel ................ 435/23

OTHER PUBLICATIONS

Methods of Enzymatic Analysis, Third Edition,(Ed.-in-chief: H. V. Bergmeyer, Verlag Chemie GmbH, Weinheim FRG (1983), vol. II, pp. 26–83.

Primary Examiner—Jeffrey E. Russel
Assistant Examiner—Ralph Gitomer
Attorney, Agent, or Firm—Steinberg, Raskin & Davidson

[57] ABSTRACT

A method, reagent mixture and test kit are provided for testing a urine sample for the presence of bacterial or somatic cells, by reacting a urine sample with a catalase-free alkaline protease enzyme and a detergent compatible therewith, so as to disrupt any such cells present in the sample and release active catalase therefrom. The presence of catalase is detected by the formation of foam upon the addition of $H_2O_2$. The reaction of the sample with the protease enzyme and the detergent is conducted in the presence of: (a) a buffer providing for a pH of about 8.5 to about 9; and optionally (b) one or more additional solutes; the total concentration of components (a) and (b), when present, being from about 0.02M to about 0.4M.

11 Claims, No Drawings

METHOD, REAGENT MIXTURE AND KIT FOR DETERMINING THE PRESENCE OF BACTERIAL OR SOMATIC CELLS IN URINE

The present specification is a continuation-in-part of pending U.S. Ser. No. 07/676864 filed Mar. 28, 1991 now abandoned which is a continuation of abandoned U.S. Ser. No. 07/548,023 filed Jul. 5, 1990, which in turn was a continuation of abandoned U.S. Ser. No. 07/065,315 filed Jun. 22, 1987.

The present invention relates to a method for testing a urine sample for the presence of bacterial or somatic cells. More particularly, the present invention provides a highly sensitive method, reagent and test kit for rapid detection of catalase in urine which is an indication for the presence of bacterial or somatic cells in the urine.

As is known, clean, healthy urine has no catalase activity. The presence of catalase indicates that the urine is contaminated or colonized by bacteria or that a pathological condition exists that has to be investigated. The common pathological conditions indicated by catalase activity in urine include significant asymptomatic bacteriuria, pyuria, hematuria and tissue damage from the kidney down to the urinary tract.

The diagnosis of any of the above conditions is based on well established laboratory procedures which must continue to provide the sole, reliable basis for a positive diagnosis. The present invention provides a method and test kit designed for fast screening of a large number of urine samples and discarding healthy urines that need not be investigated for any of the above mentioned pathological conditions. It may be used as a screening test for surveying a presumably healthy population, e.g., in schools and other institutions, where a screening program for asymptomatic bacteriuria is occasionally conducted. It may also serve as a preliminary screening of a large number of urines received for routine examination in large diagnostic laboratories. Specimens found to be negative by the present test need not be further investigated for significant bacteriuria, hematuria, pyuria or urinary tract tissue damage. The advantage of saving time, labor and cost of materials is obvious.

By using the method of the present invention, the need for incubations is completely obviated and thus the difficulties involved are eliminated. The test as described below is simple, rapid and direct. It requires no preparation, skill or equipment, and can be carried out in the physician's office or by the patient himself.

In Israel Patent Specification No. 36496, there is described and claimed a method for testing for the presence of organic cells in a liquid which comprises the steps of disrupting said cells in a sample of liquid by the combined action of a protease and detergent compatible therewith, whereby undegraded desoxyribonucleic acid (DNA) and active enzymes are released, and thereafter testing said sample for the presence of DNA and/or of a released enzyme.

In preferred embodiments of said patent said liquid is urine and said cells are bacterial cells, and the released enzyme is catalase which is tested for by its reaction with $H_2O_2$ to release gaseous oxygen with resultant formation of foam. In this test, the assay of catalase activity follows the treatment of the specimen with a cell disrupting preparation. The treatment is intended to remove possible accessibility barriers between catalase present inside cells and its substrate. The presence of such barriers will slow down catalytic reaction and thus interfere with the detection of catalase. Disruption of cells is thus intended for making the total catalase content of the specimen instantly detectable.

As described and explained in said patent, although disruption of bacterial cells can be accomplished by several well-known procedures, none of these is acceptable for the present purpose. The available methods are usually laborious and time-consuming, or else not generally effective. The most reliable methods of disruption depend on the use of expensive equipment (e.g. mechanical, sonic or ultrasonic disintegrators).

The addition of the protease and detergent to a sample of urine was found to cause maximal exposure of intra-cellular bacterial enzymes present in that sample within 5 minutes at room temperature, and more rapidly at higher temperatures. The protease-detergent disrupting agent acts rapidly under near to physiological conditions of pH and temperature, and was believed not to interfere with the detection of the catalase released by the treatment.

Initial studies summarized in said patent, confirmed that disruption increases the sensitivity of catalase detection to the point where it can be used for rapid screening of urine. The results of an evaluation of prototype strip test constructed on the above principle are given in Table II of said patent.

Further testing, however, of larger numbers of specimens (750 vs. 162 urine specimens) in a routine diagnostic laboratory yielded less satisfactory results with a specificity of only 65% and 35% false positives and 21% false negatives.

Thus, when an attempt was made to commercialize the test described and claimed in said patent it was realized that the preferred embodiment exemplified in said patent was not sensitive enough, as indicated by the unacceptably high rate of both false positive and false negative results.

Repeated attempts to refine the test and eliminate the causes for the false positives and false negatives met with repeated failure. Furthermore, it also became clear, following a careful and detailed study of said patent that there were no clues in that document that would help in tracing the roots of the problem or suggest a solution. Therefore said method and said patent were abandoned.

Only ten years later was said method once again considered, however, since said patent provided no clues as to an obvious remedy to the problem which resulted in the original abandonment of said patent, further extensive research was necessary and directed to the design of a modified method and test kit which would yield unambiguous results. The specific aims of the subsequent research were to determine if it was possible to:

(a) Increase sensitivity, so as to ensure clear response of positive specimens;

(b) Eliminate irrelevant positive-characterizing foam-formation, so as to avoid spurious responses in negative specimens and thereby reduce the unacceptably high level of false positive scoring which was found in the prior method.

A large series of potentially useful combinations of proteases and compatible detergents was investigated. These included both ready-made commercial preparations and experimental combinations of technical grade enzyme preparations and detergents. It turned out that the requirement for an effective cell disrupting preparation imposed severe limitations on the choice of reagents. Laboratory made preparations were invariably inferior to the commercial preparations, mainly for reasons of enzyme-detergent incompatability. On the other hand commercial preparations, including that specified in the Patent continued to give high false positive results.

Furthermore the even more troublesome problem of an unacceptably high rate of false negative results persisted.

A major breakthrough occurred from a chance and surprising observation which contradicted the conventional wisdom of those in the field. It was surprisingly found that the mistaken addition of urea to the urine testing solution resulted in a greater release of trapped oxygen. Other solutes were tested and found to be equally effective to achieve this result and thus a method and means were found to eliminate the false negative results obtained following the teaching of Israel patent 36496.

This discovery was unexpected and surprising for two reasons. First, while it is known and described in the literature, e.g., in U.S. Pat. No. 4,116,773 that if a salt or combination of salts is included in enzyme reagents which react with oxygen in samples containing enzyme substrates to be measured in the solubility of oxygen in the reagent is reduced, such references teach the inclusion of such salts in quantities sufficient to reduce the solubility of oxygen in the reagent when compared to the solubility of oxygen in water. In the present invention however the prior and present test medium is a urine sample which is known to be rich itself in solute, Thus considering the relatively high percentage of natural solute in urine it was not and would not have been expected that the addition of further solutes would be necessary or have any appreciable effect.

This Israel Patent 36496 teaches and exemplifies buffering with 0.01M phosphate to achieve a pH of 7.5 and before the present invention it was not obvious even to the inventor thereof that the addition of further solutes would solve one of the problems which caused the original test and kit to be abandoned. Secondly according to the conventional wisdom, and as also believed by the present inventor at said time it was desirable to keep the buffer concentration to the minimum necessary to achieve the desired pH since buffers act as solutes and solutes interfere with cell description.

This conventional wisdom is reflected inter alia by Methods of Enzymatic Analysis, Third Edition, (Ed.-in-chief: H. V. Bergmeyer, Verlag Chemie GmbH, Weinheim, FRG (1983), Volume II, pp. 66–73. As explained by Bergmeyer, solutes are recommended for osmotic protection of components of disrupted cell preparation. For bacterial cells, which are the main concern here, the classical example is the procedure for creating and maintaining protoplasts (or spheroplasts) from disrupted bacteria. The procedure requires addition of solutes (sugars or salts) to the disruption medium in order to maintain the protoplasts intact. Anyone who has studied bacteriology or microbiology at any level will remember this as one of the basic observations he has made, He will also know that the intracellular enzymes, such as catalase, will remain trapped in the intact protoplast. Thus he will assume that the addition of solutes will act to prevent the release of the enzyme, and thus interfere with the proposed testing method.

Thus in contradistinction to the teaching of Israel Patent 36496 of the addition of only 0.01M phosphate buffer and the state of the art which suggested, and from which it was assumed, that addition of solutes would be counterproductive in the context of the present testing method it has been surprisingly discovered that the presence at least 20 mM of a pH buffer, said buffer being present alone or in combination with one or more additional solutes, results in the reduction of the solubility of oxygen in solution thereby eliminating false negatives while not interfering with the release of catalase.

Preferably, the total concentration of said buffer, and said solutes when present are from about 0.02M to about 0.4M and especially preferred in the use of about 30 to 70 mM of a pH buffer and about 30 to 70 mM of an additional solute.

A further basis of the present invention was the surprising discovery that one of the reasons for the false positive results when using the teaching of the Israeli Patent, was the presence of bacterial cells in the alkaline protease enzyme enriched detergent BIOOR used at the time. Thus it has been found that contrary to the teachings of Israeli Patent 39496 it is not sufficient to utilize the cell disrupting activity of a protease and a detergent compatible therewith and that even the preferred enzyme enriched washing powder marketed in the name BIOOR by Shemen Ltd. Haifa Israel, exemplified in said Patent in fact does not give satisfactory results. Instead there must be used a substantially catalase free alkaline protease enzyme enriched detergent.

While such a requirement might appear in hindsight to be self-evident, the contamination of BIOOR, which was used and taught as the preferred embodiment in said Patent, was never suspected and as a matter of fact was unexpected because alkaline protease is prepared from culture supernatants of *Bacillus subtilis*, whereas catalase is not secreted and therefore its presence must indicate inadvertent contamination with the bacterial cells. It is now known that the BIOOR preparations have been and still are unreliable for the present purpose because of the ever-present risk of significant contamination.

Up to the time, however that the present invention was made, one skilled in the art would have had no reason to expect that only specially prepared materials as described hereinafter, or the enzyme enriched washing powders BIOMAT made by Witco Chemical Ltd., Haifa, Israel, would eliminate the deficiencies of the prior art process.

Thus according to the present invention there is now provided a method for testing a urine sample for the presence of bacterial or somatic cells comprising reacting said sample in solution with a substantially catalase-free alkaline protease enzyme and a detergent compatible therewith in the presence of hydrogen peroxide and in the presence of at least 20mM of a pH buffer, said buffer being present alone or in combination with one or more additional solutes capable of reducing the solubility of oxygen in solution, the total concentration of said buffer and said solutes, when present, being from about 0.02M to about 0.4M to form an admixture for a time and under conditions sufficient to disrupt any such cells present in the sample and release active catalase therefrom, thereafter determining the presence of catalase in said sample by visually observing the extent of foam generated in said admixture, said buffer, and said solute when present, serving to increase the amount of released oxygen available to generate said foam.

In preferred embodiments of the present invention said buffer is selected from the group consisting of Tris, phosphate salts, borate salts and combinations thereof and said additional solute is selected from the group consisting of inorganic salts, organic polyols, monosaccharides, disaccharides and urea.

In especially preferred embodiments of the present invention said additional solute is selected from the group consisting of phosphate, sulfate and chloride salts.

Preferably said buffer is Tris, present at a concentration of preferably about 30–70 mM, and said additional solute is $K_2HPO_4$ present at a concentration of preferably 30–70 mM. Other suitable buffers are phosphate salts and borate salts.

Other highly soluble inorganic salts (e.g. ammonium sulfate, sodium chloride, potassium chloride, magnesium chloride etc.) as well as soluble organic compounds (e.g. ureas, polyols, monosaccharides, sucrose etc.) can be used as said additional solute at sufficiently high concentrations in addition to said buffers to expel dissolved oxygen.

Since in accordance with the present invention at least twice as much and preferably even more than 5 times as much buffer is added alone or in combination with one or more additional solutes capable of reducing the solubility of oxygen in urine, the sensitivity of the test is increased even more due to the fact that all oxygen generated by the catalase reaction enters into the foam generating process. Israel Patent No. 36496 states that the method described and claimed therein permits the detection of $50-100 \times 10^3$ bacteria in 1 ml of sample. As shown by the Examples hereinbelow, the improved method of the present invention exhibits a significantly higher sensitivity, by about one order of magnitude as compared to the method of said Patent. This increased sensitivity meets the requirements of physicians and medical institutions.

In another aspect of the present invention, there is provided a reagent mixture for carrying out the method of the invention, which mixture comprises a reagent mixture for carrying out the method of claim 1 which comprises at least one catalase-free alkaline protease enzyme, a detergent compatible with said enzyme, and at least 20mM of a pH buffer, said buffer being present alone or in combination with one or more additional solute capable of reducing the solubility of oxygen in solution, the total concentration of said buffer, and said solute when present, being from about 0.02M to about 0.4M.

The reagent mixture according to this aspect of the invention may preferably comprise also a dye which serves as a dark background for a clearer detection of the pale foam. The reagent mixture may be in the form of an aqueous solution wherein the concentrations of the buffer and the additional solute (or solutes), when present, are such that when a predetermined volume of said solution is mixed with a predetermined volume of urine sample and a predetermined volume of an aqueous $H_2O_2$ solution, the resultant solution will have a pH of about 8.5 to 9.0 and a total concentration of said buffer and said additional solute (or solutes), when present, from about 0.02M to about 0.4M. This aqueous solution may further comprise one or more preserving agents and/or stabilizers in order to prolong its shelf life.

Alternatively and preferably, the reagent mixture according to the invention may be in dry form, i.e. in the form of a powder which, when a predetermined amount thereof is mixed with a predetermined volume of a urine sample and a predetermined volume of an aqueous $H_2O_2$ solution, will provide for a pH of about 8.5 to 9.0 in the resultant solution and a total concentration of buffer and additional solute (or solutes), when present, of about 60 to 140 mM.

In yet another aspect of the invention there is provided a test kit for carrying out the method of the invention, the kit comprising, a plurality of test tubes suitably graduated so as to enable the addition thereto of a predetermined volume of urine and a predetermined volume of an aqueous $H_2O_2$ solution, each of said test tubes containing a reagent mixture which comprises at least one catalase-free alkaline protease enzyme, a detergent compatible with said enzyme, and at least 20 mM of a pH buffer, said buffer being present alone or in combination with one or more additional solutes capable of reducing the solubility of oxygen in solution, the total concentration of said buffer, and said solute when present, being from about 0.01M to about 0.4M.

The test kit according to the invention may optionally comprise also a packaged aqueous $H_2O_2$ solution.

While the invention will now be described in connection with certain preferred embodiments in the following examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Detection of Cells in Urine

Materials

Test Tubes

Tris buffer, purchased from "Serva".

Giemsa Stain and Hydrogen Peroxide (30%) products of BDH Chemicals Ltd.

BM powder (BIOMAT)*, marketed by WITCO Chemical Ltd. P. O. Box 975, Haifa 31009.

* (Enzyme-enriched washing powder. The enzyme is an alkaline protease produced by a Carlsberg Strain of *Bacillus subtilis* and marketed under the name of Alkalase or Subtilisin.)

Methods

I. Preparation of reagents
a) A 3M solution (a) of Tris in distilled water (pH 9.0) was prepared.
b) The Giemsa stain was diluted 1:25 in distilled water to form solution (b).
c) The Tris solution (a) and the Giemsa stain solution (b) were mixed in a 1:1 ratio.
d) BM powder was ground together with an equal weight of $K^2HPO^4$ and the resulting powder mix stored at room temperature.

II. Testing of Urine
a) 15 mg of the powder mix was placed at the bottom of a test tube.

b) 0.05 ml of the Tris and Giemsa solution (1:1) were added.
c) 1 ml of urine was added.
d) 0.20 ml of $H_2O_2$ (6%) was added to start the reaction i.e. the development of foam.
e) When a pronounced ring of foam was observed after 5 minutes, the urine was scored as positive. The foam formed was stable for 1-2 hours, or sometimes more.

Almost 1500 clinical urine samples were tested both in accordance with the above procedure and by conventional clinical laboratory methods (e.g. bacterial colony counting). The results are summarized in the following Table I.

TABLE I

|  | Series I (Dec. 85–Feb. 86) | Series II (March 1986) |
| --- | --- | --- |
| Total No. | 925 | 571 |
| True positives | 366 | 240 |
| False positives | 82 | 50 |
| True negatives | 467 | 273 |
| False negatives | 10 | 8 |
| Sensitivity[a] | 97.3 | 96.7 |
| Specificity[b] | 85.0 | 84.5 |
| Pos. predictive value[c] | 81.6 | 82.7 |
| Neg. predictive value[d] | 97.9 | 97.1 |

$$(a) \frac{\text{true positives}}{\text{true positives + false negatives}} \times 100$$

$$(b) \frac{\text{true negatives}}{\text{true negatives + false positives}} \times 100$$

$$(c) \frac{\text{true positives}}{\text{true positives + false positives}} \times 100$$

$$(d) \frac{\text{true negatives}}{\text{true negatives + false negatives}} \times 100$$

The visual determination of the positive reaction is facilitated by:
1) the detergent, which participates in the disruption of the cells, and is also suitable for providing a foam layer which forms when oxygen is released from hydrogen peroxide by the action of catalase; and
2) the dye (e.g. Giemsa Stain) which provides a dark background against which the foaming (Positive reaction) is clearly visible.

The above procedure therefore satisfied the requirements for a rapid and reliable test for bacterial of somatic cells in urine. Furthermore, the addition of both solid $K_2HPO_4$ and Tris serves a dual purpose: They act as a buffer, so that all urine specimens are examined at the optimal pH, and they also serve to decrease the solubility of the oxygen released by the catalase reaction with $H_2O_2$, thereby enhancing the sensitivity of the test.

COMPARATIVE EXAMPLE 2

Demonstration of the Increased Sensitivity Provided by the Addition of a Solute (Tris) to Urine Nine different, catalase-positive samples of urine were tested as follows. Each sample was tested twice, namely (A) at a low molarity (10 mM) and (B) at a high molarity (110 mM) of the solutes added with the BIOMAT powder. The pH of all samples in (A) and (B) was identical, and the composition of the reagents was identical except for the amount of Tris buffer which was increased in (B) so as to increase the molarity to 110 mM in that series. The results in Table II are expressed as the height of foam (in cm.), produced at the end of the test. While the composition and content of different urine samples will cause variations in the extent of release of oxygen, in 8 out of the 9 samples tested the release of oxygen has been found to respond to the added solute (Tris) to a remarkable degree.

TABLE II

| SAMPLE NO. | A | B |
| --- | --- | --- |
| 1 | 5.0 | 4.9 |
| 2 | 3.4 | 4.5 |
| 3 | 2.4 | 4.05 |
| 4 | 1.9 | 4.05 |
| 5 | 1.9 | 3.95 |
| 6 | 1.9 | 3.4 |
| 7 | 1.5 | 3.15 |
| 8 | 1.5 | 3.1 |
| 9 | 1.5 | 3.6 |

It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein. made to the appended claims, rather than to the foregoing description, and all changes which come within the meaning and range of equivalency of the claims are therefore intended to be embraced therein.

What is claimed is:

1. A method for testing a urine sample for the presence of catalase as an indicator of the presence of bacterial or somatic cells comprising reacting said sample in solution with a substantially catalase-free alkaline protease enzyme produced by *Bacillus subtilis* and a detergent compatible therewith in the presence of hydrogen peroxide and at least 20 mM of a pH buffer which acts as a solute, said buffer being present alone or in combination with one or more additional solutes which reduce the solubility of oxygen in solution, the solution of said buffer and said one or more additional solutes, when present, having a pH in the range of 7.5–9.0, and the total concentration of said buffer and said one or more additional solutes, when present, being from about 0.02M to about 0.4M to form an admixture which is maintained under conditions and for a time sufficient to disrupt any such cells present in the sample and release active catalase therefrom, thereafter determining the presence of catalase in said sample by visually observing the extent of foam generated in said admixture, said buffer and said one or more additional solutes, when present, serving to increase the amount of released oxygen available to generate said foam.

2. The method according to claim 1 wherein said buffer is selected from the group consisting of Tris, phosphate salts, borate salts and combinations thereof.

3. The method according to claim 1 wherein said one or more additional solutes are selected from the group consisting of inorganic salts, organic polyols, monosaccharides, disaccharides and urea.

4. The method according to claim 3 wherein said additional solutes are selected from the group consisting of phosphate, sulfate and chloride salts.

5. A test kit for carrying out the method of claim 1, comprising a plurality of test tubes suitably graduated so as to enable the addition thereto of a predetermined volume of urine and a predetermined volume of an aqueous $H_2O_2$ solution, each of said test tubes containing a reagent mixture which comprises at least one catalase-free alkaline protease enzyme produced by *Bacillus subtilis*, a detergent compatible with said at least one enzyme, and at least 20 mM of a pH buffer which acts as a solute, said buffer being present alone or in combination with one or more additional solutes which reduce the solubility of oxygen in solution, the solution of said buffer and said one or more additional solutes, when present, having a pH in the range of 7.5–9.0, and the total concentration of said buffer, and said one or more additional solutes, when present, being from about 0.02M to about 0.4M.

6. A reagent mixture for carrying out the method of claim 1 which comprises at least one catalase-free alkaline protease enzyme produced by *Bacillus subtilis*, a detergent compatible with said at least one enzyme, and at least 20 mM of a pH buffer which acts as a solute, said buffer being present alone or in combination with one or more additional solutes which reduce the solubility of oxygen in solution, the solution of said buffer and said one or more additional solutes, when present, having a pH in the range of 7.5–9.0, and the total concentration of said buffer, and said one or more additional solutes, when present, being from about 0.02M to 0.4M.

7. The reagent mixture of claim 6 comprising about 30 to 70 mM of acid pH buffer and about 30 to 70 mM of said one or more additional solutes.

8. The reagent mixture of claim 6 wherein said buffer is selected from the group consisting of Tris, phosphate salts, borate salts and combinations thereof.

9. The reagent mixture of claim 6 wherein said one or more additional solutes are selected from the group consisting of inorganic salts, organic polyols, monosaccharides, disaccharides and urea.

10. The reagent mixture of claim 6 wherein said one or more additional solutes are selected from the group consisting of phosphate, sulfate and chloride salts.

11. The reagent mixture of claim 6 wherein said catalase-free alkaline protease is enriched with a detergent which is capable of foaming.

* * * * *